United States Patent
Gaska et al.

(10) Patent No.: US 12,377,179 B2
(45) Date of Patent: Aug. 5, 2025

(54) UV DISINFECTION DEVICE AND METHOD

(71) Applicant: Uvton, Inc., Columbia, SC (US)

(72) Inventors: Remigijus Gaska, Columbia, SC (US); Igor Agafonov, Columbia, SC (US)

(73) Assignee: Uvton, Inc., Columbia, SC (US)

( * ) Notice: Subject to any disclaimer, the term of this patent is extended or adjusted under 35 U.S.C. 154(b) by 942 days.

(21) Appl. No.: 17/374,242

(22) Filed: Jul. 13, 2021

(65) Prior Publication Data

US 2022/0016283 A1 Jan. 20, 2022

Related U.S. Application Data

(60) Provisional application No. 63/053,105, filed on Jul. 17, 2020.

(51) Int. Cl.
*A61L 2/10* (2006.01)
*A61L 2/26* (2006.01)

(52) U.S. Cl.
CPC ...... *A61L 2/10* (2013.01); *A61L 2/26* (2013.01); *A61L 2202/122* (2013.01); *A61L 2202/15* (2013.01); *A61L 2202/20* (2013.01)

(58) Field of Classification Search
CPC .......... A61L 2/10; A61L 2/26; A61L 2202/11; A61L 2202/121; A61L 2202/122
See application file for complete search history.

(56) References Cited

U.S. PATENT DOCUMENTS

| | | |
|---|---|---|
| 3,955,922 A | 5/1976 | Moulthrop |
| 4,448,750 A | 5/1984 | Fuesting |
| 5,225,172 A | 7/1993 | Meyler et al. |
| 5,852,879 A | 12/1998 | Schumaier |
| 7,692,159 B2 | 4/2010 | Lane et al. |
| 2010/0326584 A1 | 12/2010 | Schibsbye |
| 2017/0319725 A1* | 11/2017 | Hann ........................ A61L 2/10 |

(Continued)

FOREIGN PATENT DOCUMENTS

KR 102054265 B1 * 12/2019

OTHER PUBLICATIONS

English-language machine translation of KR-102054265-B1 (Year: 2019).*

(Continued)

*Primary Examiner* — Timothy C Cleveland
(74) *Attorney, Agent, or Firm* — JK Intellectual Property Law, PA

(57) ABSTRACT

A device for cleaning a target may include a housing including a base and a lid; a chamber within the housing having a top within the lid, a bottom within the base, and at least one UV reflective plate; at least one UV emitter attached to the housing and positioned to emit UV radiation into the chamber; and a support attached to the housing and located in the chamber, the support configured for locating the target so that the UV radiation illuminates the target. All of the at least one UV emitters may be located in the base of the housing and none of the at least one UV emitters may be located in the lid of the housing. A means may be provided for rotating the support relative to the base so that the target moves relative to the at least one UV emitter. The means may include at least one of a fan, a motor, and actuator, and/or specially-configured support plates, and/or bases of housings.

19 Claims, 15 Drawing Sheets

(56) References Cited

U.S. PATENT DOCUMENTS

2019/0167827 A1 6/2019 Gaska et al.
2022/0125969 A1 4/2022 Gaska et al.

OTHER PUBLICATIONS

Casado, et al. "Design and validation of a LED-based high intensity photocatalytic reactor for quantifying activity measurements", Chemical Engineering Journal, 327 (2017) 1043-1055.

* cited by examiner

UV DISINFECTION DEVICE AND METHOD

CROSS-REFERENCE TO RELATED APPLICATIONS

This application claims benefit to U.S. Provisional Patent Application No. 63/053,105, filed Jul. 17, 2020, which is incorporated by reference herein in their entireties.

TECHNICAL FIELD

The present disclosure relates generally to ultraviolet radiation, and more particularly, to a device and method for disinfection of a target, such as a sound transmission device, and the like, using ultraviolet radiation.

BACKGROUND

Reliable disinfection of sound transmission devices, such as hearing aid devices, wired and wireless transmitter/receivers including earphones, earbuds, and Bluetooth devices, etc., is a major problem. Chemical treatment using various disinfecting liquids is usually selective and eradicates some microorganisms but not all. However, chemical treatment may undesirably alter surface properties of the items under treatment. Chemical treatment without submersion and using wipes is complicated, especially for small items.

Ultraviolet (UV) radiation may be used to disinfect and operates by damaging and/or destroying DNA in a non-selective way. Different microorganisms have different doses for eradication. Eradication of microorganisms is achieved by controlling ultraviolet radiation doses to make them sufficient for eradication of most ultraviolet resistant species. Most common sources of ultraviolet light for disinfection are various lamps, primarily Mercury lamps. Disinfection devices based on Mercury lamps are bulky and can only be used as desktop devices. They generate large amounts of heat which limits disinfection exposure time and distance from irradiated object, which, in turn imposes minimum critical footprint of the devices. Mercury lamps contain hazardous materials (Mercury), use high voltage and are easy to break causing spill of Mercury and contamination of disinfection devices and irradiated objects. Sensitivity of the lamps to mechanical stress limit use of disinfection devices for travel and outdoors.

Surfaces of objects can be processed using ultraviolet light as a germicidal medium to reduce the microbial load. Water and air have been treated with ultraviolet light for quite some time to provide safe drinking water and eliminate air-borne infections and harmful pathogens. High power ultraviolet lamps have been used to disinfect surgery rooms in hospitals and sterilize medical instruments. All these applications use a variety of ultraviolet lamps, primarily low-pressure and medium-pressure Mercury lamps ranging from compact lamps for water treatment outdoors and disinfecting small devices such as HADs to massive lamp assemblies used in municipal water treatment plants. Use of such ultraviolet lamps requires complex electronics for ignition and stable operation of these high-voltage and temperature-sensitive light sources that need a significant warm up time to become fully operational. They also require special safety and handling procedures, especially during maintenance and replacement process in order to prevent glass breakup and contamination of environment with hazardous materials.

UV LED's can also be used to kill microorganisms. Peak emission wavelength of UV LED's can be adjusted during manufacturing process to provide an optimal irradiation band for eradication of specific bacteria, viruses, mold and fungi. In general, ultraviolet light is classified into three wavelength ranges: UV-C, from about 200 nanometers (nm) to about 280 nm; UV-B, from about 280 nm to about 320 nm; and UV-A, from about 320 nm to about 400 nm. Generally, ultraviolet light, and in particular, UV-C light is "germicidal," i.e., it deactivates the DNA of bacteria, viruses and other pathogens and thus destroys their ability to multiply and cause infections and diseases. This effectively results in eradication of the microorganisms. Specifically, UV-C light causes damage to the nucleic acid of microorganisms by forming covalent bonds between certain adjacent bases in the DNA. The formation of these bonds prevents the DNA from replication, and the organism is neither able to produce molecules essential for life process, nor is it able to reproduce. In fact, when an organism is unable to produce these essential molecules or is unable to replicate, it becomes harmless.

While existing devices work for their intended purposes, it can be difficult to effectively clean all surfaces of a complex-shaped target item that may be shaped for placement on or in a user's ear without employing many LED devices, movable LED devices, complex light delivery systems, etc. Accordingly, a UV disinfection device and method that were simple, cost effective, energy efficient, or that addressed one of the drawbacks of existing disinfection systems or other issue would be welcome.

SUMMARY

According to certain aspects of the disclosure, various aspects of devices and methods and provided for disinfecting and/or and drying target items placed within a chamber of a disinfecting device. In embodiments disclosed herein, an ultraviolet autonomous device uses UV radiation provided by UV emitters, which may be LED's, super-luminescent LED's, laser diodes, or other UV emitters.

According to one aspect of the disclosure, a device for cleaning a target may include a housing including a base and a lid; a chamber within the housing having a top within the lid, a bottom within the base, and at least one UV reflective plate; at least one UV emitter attached to the housing and positioned to emit UV radiation into the chamber, all of the at least one UV emitters being located in the base of the housing and none of the at least one UV emitters being located in the lid of the housing; and a support attached to the housing and located in the chamber, the support configured for locating the target so that the UV radiation illuminates the target. Various options and modifications are possible.

For example, the at least one UV reflective plate may be located adjacent the top of the chamber above the support in the lid or adjacent the bottom of the chamber below the support in the base, or the at least one UV reflective plate may include a first UV reflective plate located adjacent the top of the chamber above the support in the lid and a second UV reflective plate located adjacent the bottom of the chamber below the support in the base. The base and the lid may be attached together by a hinge. At least one actuator may be provided in the base for creating vibration sufficient to move the target relative to the support.

The support may be rotatably mounted to the base, rotation of the support causing the target to be moved relative to the at least one UV emitter in the base. If so, a fan may be provided in the base for providing an airflow sufficient to rotate the support relative to the base. Also, at least one fin may be attached to a bottom surface of the support, the airflow from the fan impinging on the at least one fin to rotate the support relative to the base. Also, a motor may be provided in the base with a driven output configured for rotating the support relative to the base.

The support may include a top surface defining a depression in a center thereof configured for receiving the target and gravitationally urging the target toward a location in which the UV radiation illuminates the target.

The at least one UV emitter may include a first UV emitter centrally located beneath the support within the base and at least one second UV emitter spaced radially from the first UV emitter. If desired, three or more of the second UV emitters may be spaced around the first UV emitter. The first UV emitter and/or the second UV emitter may each include one of an LED, a UV LED, or a waveguide outlet.

According to certain other aspects of the disclosure, a device for cleaning a target may include a housing including a base and a lid; a chamber within the housing having a top within the lid, a bottom within the base, and at least one UV reflective plate; at least one UV emitter attached to the housing and positioned to emit UV radiation into the chamber; a support rotatably attached to the housing and located in the chamber, the support configured for locating the target so that the UV radiation illuminates the target; and a means for rotating the support relative to the base so that the target moves relative to the at least one UV emitter. Various options and modifications are possible.

For example, the at least one UV reflective plate may include a first UV reflective plate located adjacent the top of the chamber above the support in the lid and a second UV reflective plate located adjacent the bottom of the chamber below the support in the base.

The means for rotating may include a fan in the base for providing an airflow sufficient to rotate the support relative to the base, and may also include at least one fin attached to a bottom surface of the support, the airflow from the fan impinging on the at least one fin to rotate the support relative to the base. Alternatively, the means for rotating may include a motor in the base with a driven output configured for rotating the support relative to the base.

If desired, all of the at least one UV emitter may be located in the base of the housing and none of the at least one UV emitter may be located in the lid of the housing. Also, the at least one UV emitter may include a first UV emitter centrally located beneath the support within the base and at least one second UV emitter spaced radially from the first UV emitter.

According to other aspects of the disclosure, a device for cleaning a target may include a housing including a base and a lid; a chamber within the housing having a top within the lid, a bottom within the base, and at least one UV reflective plate; at least one UV emitter attached to the housing and positioned to emit UV radiation into the chamber; a support rotatably attached to the housing and located in the chamber, the support configured for locating the target so that the UV radiation illuminates the target, the support including at least one fin attached to a bottom surface of the support; and a fan for providing an airflow impinging on the at least one fin to rotate the support relative to the base to thereby move the target relative to the at least one UV emitter. Various options and modifications are possible.

For example, the at least one UV reflective plate may include a first UV reflective plate located adjacent the top of the chamber above the support in the lid and a second UV reflective plate located adjacent the bottom of the chamber below the support in the base. Also, all of the at least one UV emitter may be located in the base of the housing and none of the at least one UV emitter are located in the lid of the housing.

According to other aspects of the disclosure, a device for cleaning a target may include a housing including a base and a lid; a chamber within the housing having a top within the lid, a bottom within the base, and at least one UV reflective plate; at least one UV emitter attached to the housing and positioned to emit UV radiation into the chamber; a support rotatably attached to the housing and located in the chamber, the support configured for locating the target so that the UV radiation illuminates the target; and a motor in the base with a driven output configured for rotating the support relative to the base to thereby move the target relative to the at least one UV emitter. Various options and modifications are possible.

For example, the at least one UV reflective plate may include a first UV reflective plate located adjacent the top of the chamber above the support in the lid and a second UV reflective plate located adjacent the bottom of the chamber below the support in the base. Also, all of the at least one UV emitter may be located in the base of the housing and none of the at least one UV emitter may be located in the lid of the housing.

BRIEF DESCRIPTION OF THE DRAWINGS

These and other features of the disclosure will be more readily understood from the following detailed description of the various aspects of the disclosure taken in conjunction with the accompanying drawings that depict various aspects of the disclosure.

DETAILED DESCRIPTION

Figure 1:
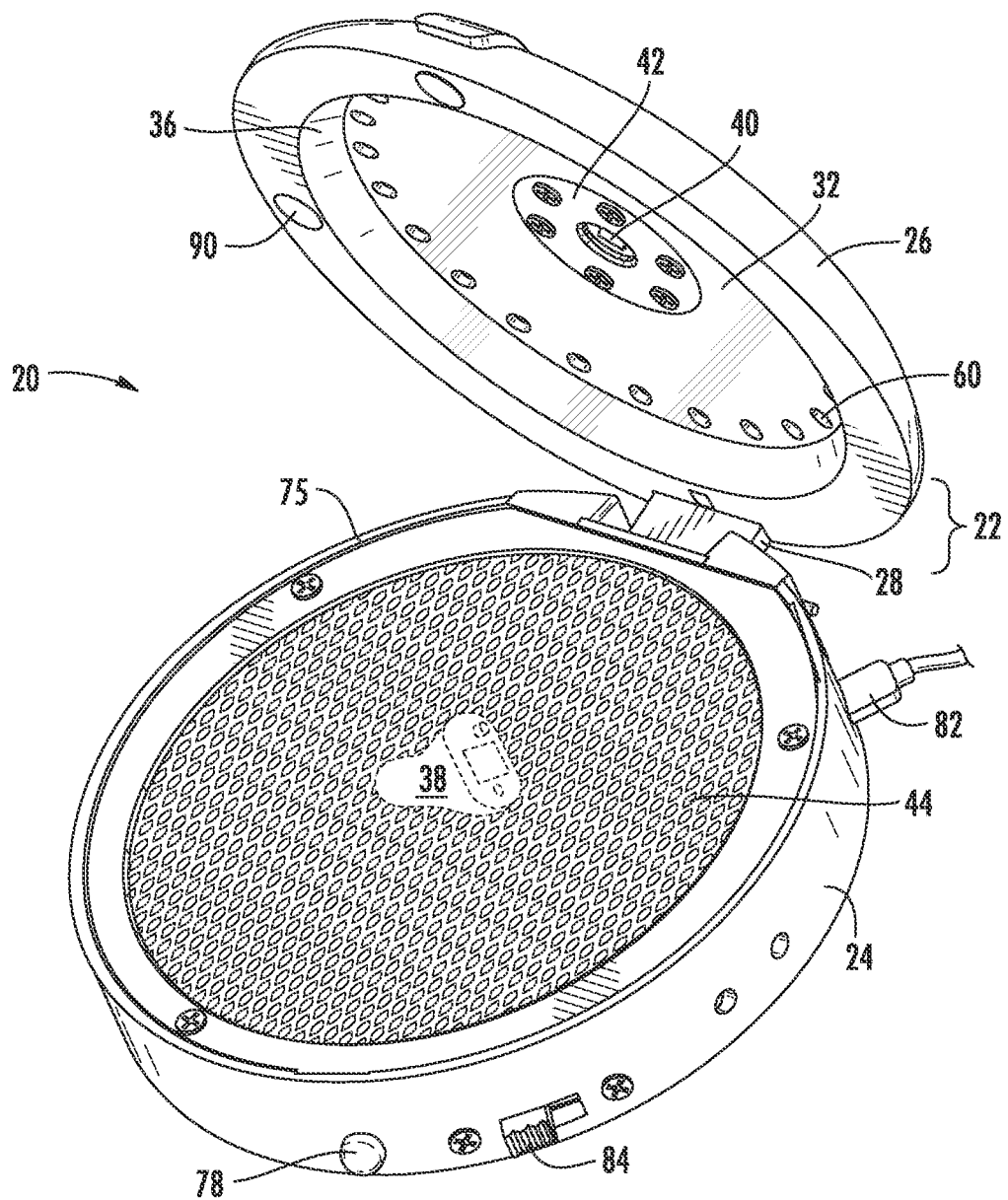
FIG. 1 is an isometric view of one example of a portable and autonomous ultraviolet disinfection and/or drying device with its lid opened, showing a UV LED mounted in the center of the device lid and a perforated support for the target item(s) to be disinfected and/or dried.
Figure 2:
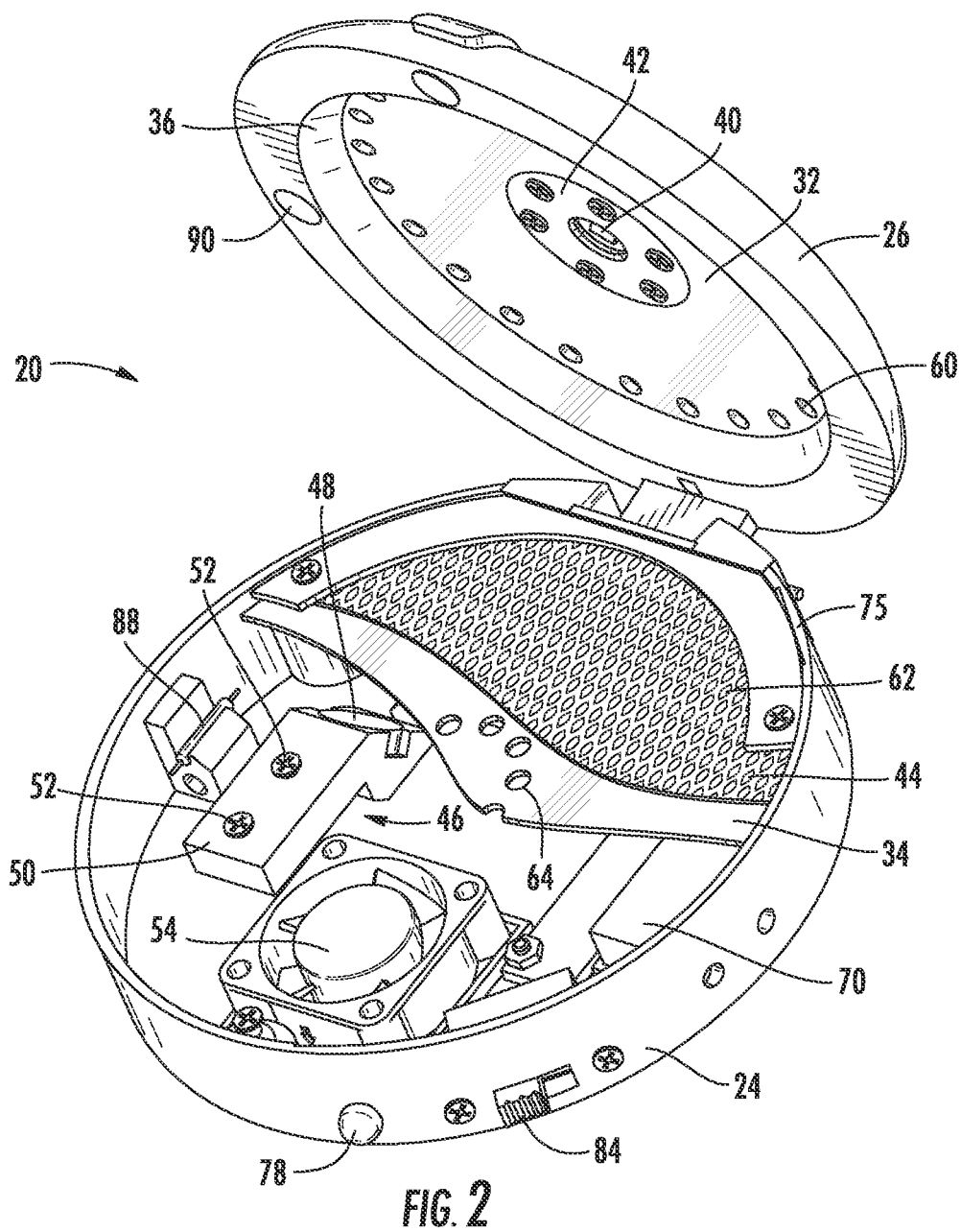
FIG. 2 is a partially broken-away isometric view of the device of FIG. 1, showing a vibration actuator, bottom UV reflective surface, air fan and other internal components.

Detailed reference will now be made to the drawings in which examples embodying the present disclosure are shown. The detailed description uses numeral and letter designations to refer to features in the drawings. Like or similar designations in the drawings and description have been used to refer to like or similar parts of the disclosure.

The drawings and detailed description provide a full and enabling description of the disclosure and the manner and process of making and using it. Each embodiment is provided by way of explanation of the subject matter not limitation thereof. In fact, it will be apparent to those skilled in the art that various modifications and variations may be made to the disclosed subject matter without departing from the scope or spirit of the disclosure. For instance, features illustrated or described as part of one embodiment may be used with another embodiment to yield a still further embodiment.

Generally speaking, the present disclosure is directed to various embodiments of a disinfection, cleaning, and/or drying device and method using UV radiation. As shown in FIGS. 1-10, a first embodiment 20 of such a device includes a housing 22 which may have a base 24, a lid 26 attached to the base by a hinge 28. Within device 20 is a chamber 30 (see FIG. 7), a first UV reflective plate 32 in lid 26, and a second UV reflective plate 34 in base 24. A third (or fourth, etc.) UV reflective surface 36 may be formed in lid 26 (as shown) or base 24 to provide a substantially continuous reflective chamber 30 for generally enveloping a target item 38 such as a sound transmission device, hearing aid device, wired and wireless transmitter/receiver, earphone, earbud, Bluetooth device, or other similar sized and/or purposed device, etc. Plates 32,34 may be curved, for example parabolic or substantially parabolic, and may have identical or differing curvature. However, one or both plates 32,34 may be flat.

At least one UV emitter, in this case an LED 40, is attached to housing 22, in this case first UV reflective plate 32, and is positioned to emit UV radiation into chamber 30. UV LED 40 may be formed in an assembly including typical electric connections and controls (not shown) and a heat sink 42 for removing heat generated by the UV LED.

A support 44 is attached to housing 22 and is located in chamber 30 between first UV reflective plate 32 and second UV reflective plate 34. Support 44 locates target 38 between first UV reflective plate 32 and second UV reflective plate 34 so that the UV radiation illuminates the target. Support 44 as shown is a perforated, mesh-like structure extending substantially across chamber 30 within base 24 when lid 26 is closed.

Figure 8:
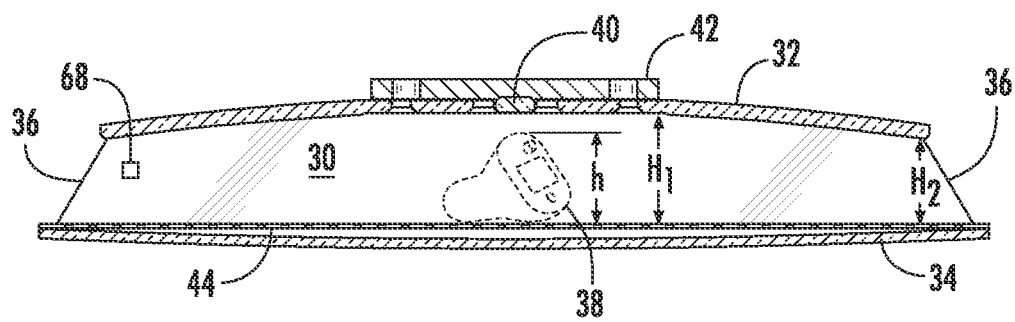
FIG. 8 is a close-up cross-sectional view of the chamber portion of FIG. 7.

As shown in FIG. 8, near the center of support 44 and UV LED 40, a spacing of a predetermined distance H1 exists between the support and top of chamber 30 (as defined here by first UV reflective plate 32). Toward the periphery of support 44, a predetermined distance H2 exists between these elements. As Illustrated, H2 is smaller than H1, as the curvature of plate 32 helps with reflection of UV radiation within chamber and toward target 32. However, plate 32 need not be used and/or need not be curved, so H2 need not be smaller than H1. As also illustrated, at least H1, and optionally both H1 and H2 may be larger than h, a height of target 32 (optionally a maximum height depending on orientation of target on support 44). Such dimensioning also assists in directing UV illumination toward and onto target 32. As discussed in more detail below, such dimensioning allows for vibrational movement of target 32 relative to support 44 UV LED 40 and chamber in general 30.

Figure 3:
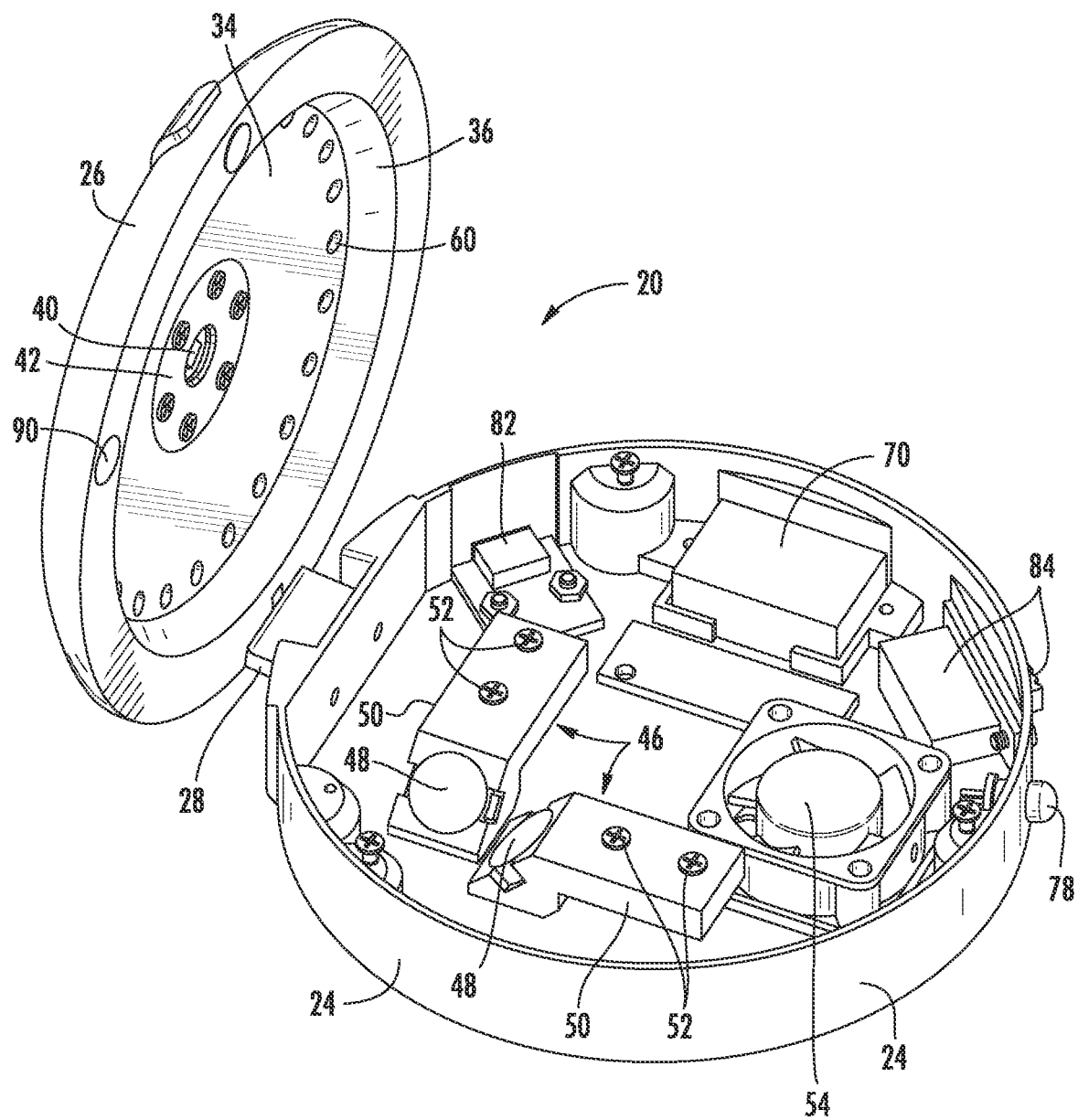
FIG. 3 is an isometric view of the device of FIG. 1, with the support and bottom UV reflective surface removed to show further internal components.
Figure 4:
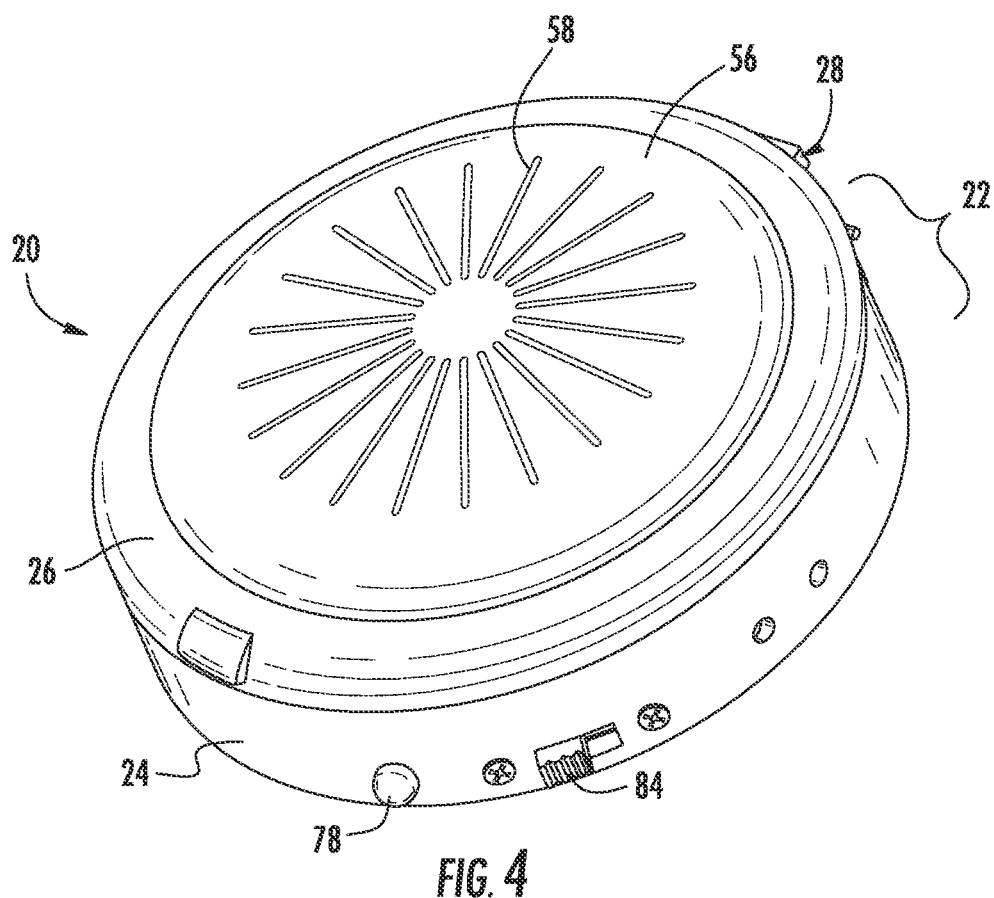
FIG. 4 is an isometric view of the device of FIG. 1, with the lid closed, showing air gaps in the cover of the lid.
Figure 5:
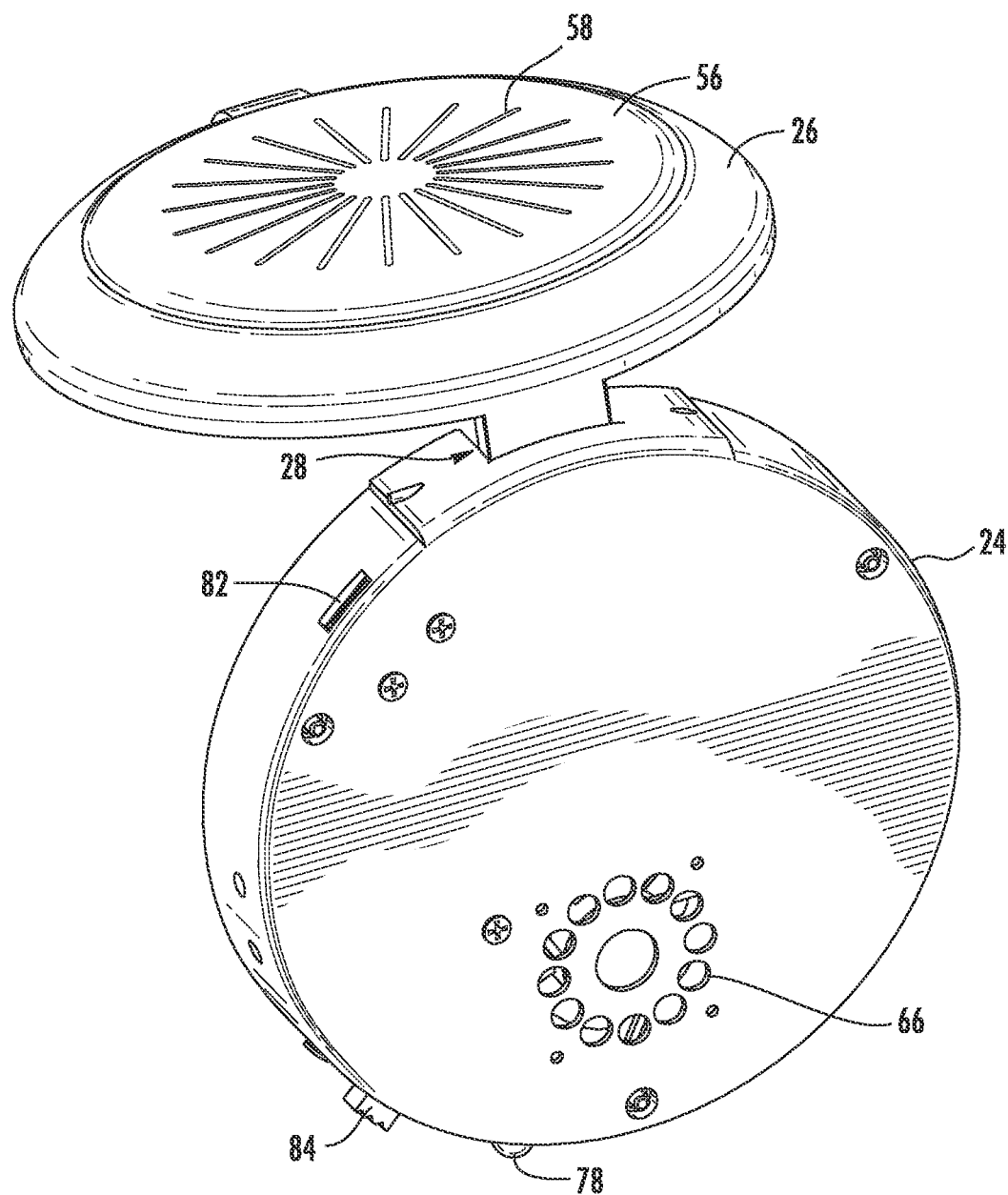
FIG. 5 is a bottom isometric view of the device of FIG. 1, showing air gaps in the bottom of the base of the device.
Figure 6:
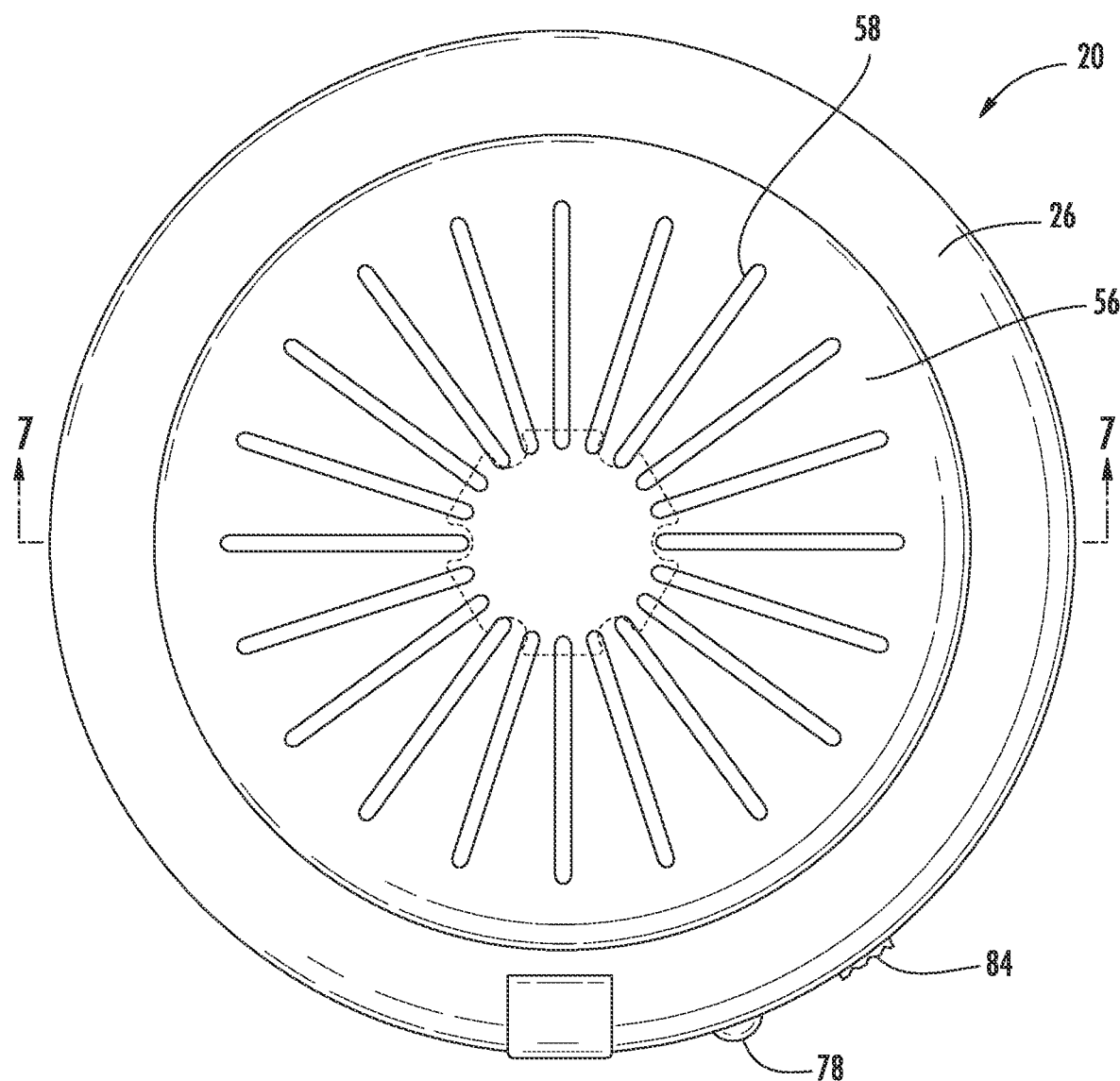
FIG. 6 is a top view of the device of FIG. 1.
Figure 7:
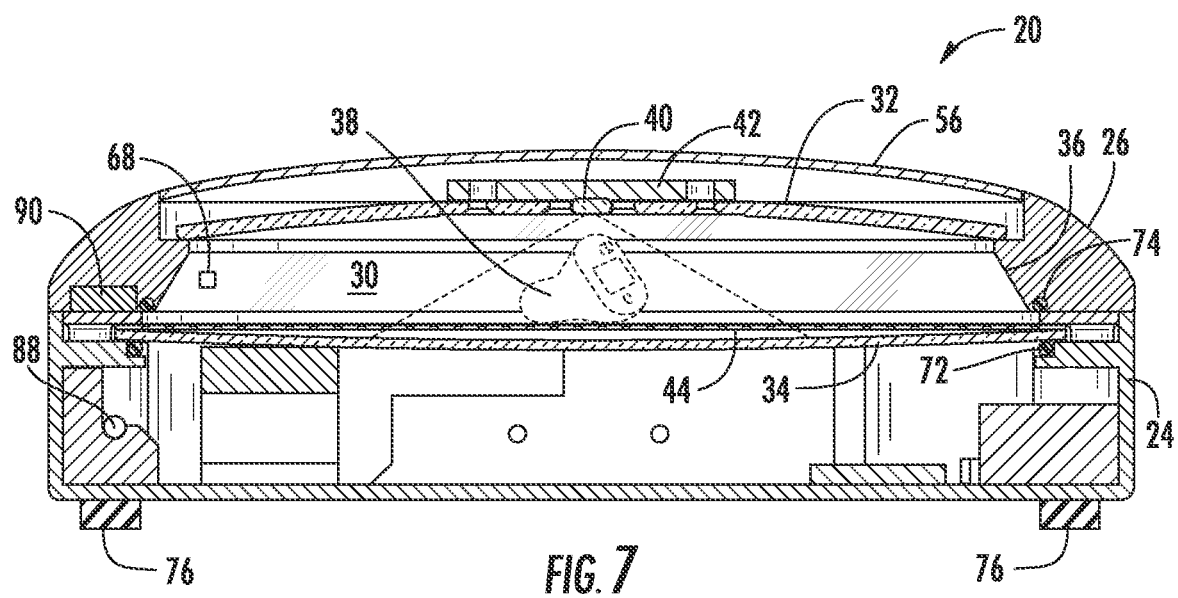
FIG. 7 is a cross-sectional view of the device of FIG. 1 taken across line 7-7 in FIG. 6, showing a chamber within the device defined by UV reflective surfaces, a UV LED and a target item on a support, and showing O-rings for radiation, moisture, and flow confinement and/or vibration control, as well as vibration control pads.
Figure 10:
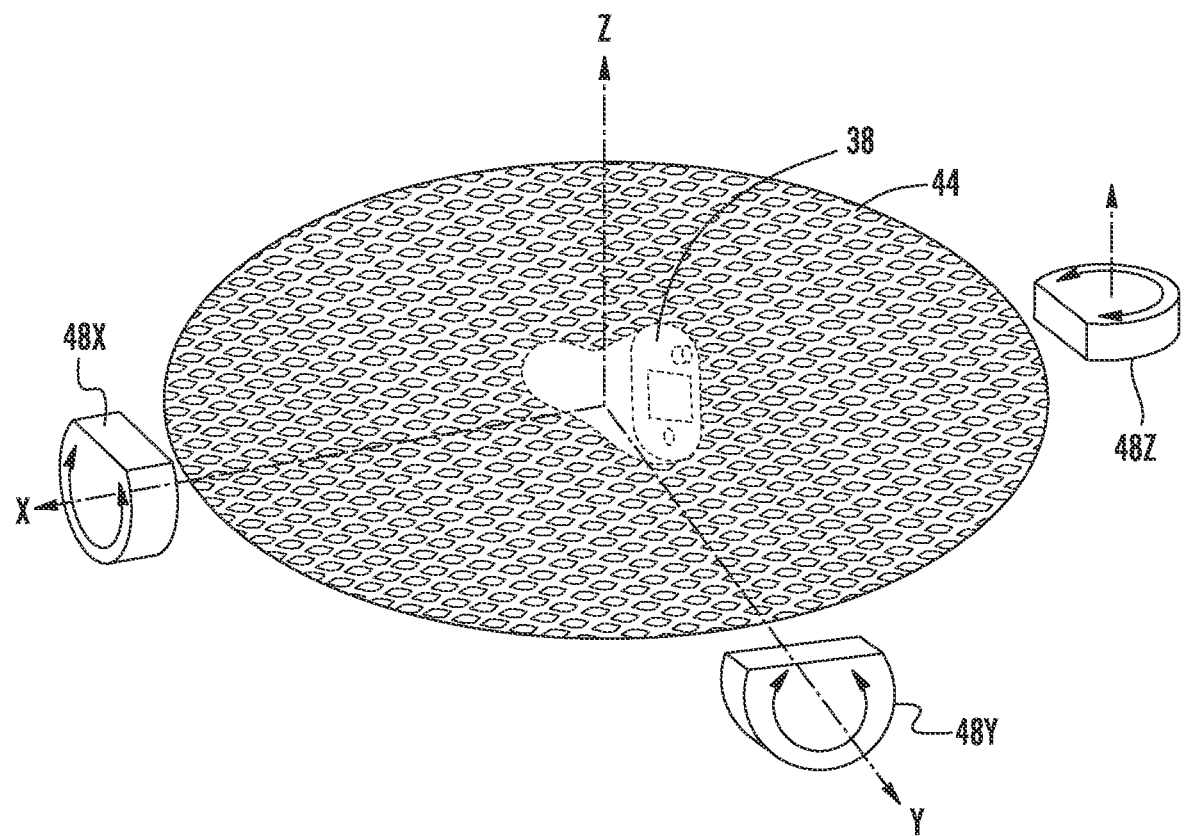
FIG. 10 is a schematic view showing that actuators may operate linearly or rotationally along three perpendicular axes relative to a target item on the support of FIG. 1.

At least one actuator 46 may be attached to housing 22, in this case base 24, and is positioned to move target 38 relative to support 44 while UV LED 40 emits UV radiation. As shown in FIG. 3, two such actuators 46 may be provided, mounted in opposing directions so as to create movement in differing planes. As illustrated, each actuator 46 may be a vibro-actuating motor 48 attached by a mount 50 to base 24, and attached to second UV reflective plate 34 by screws 52. Each vibro-actuating motor 46 may create linear motion and/or rotational motion. FIG. 10 shows three such motors 48x, 48y, and 48z, providing linear and/or rotational movement relative to the common x, y, and z axes. Alternatively, actuators 46 may also comprise piezoelectric actuators. Actuators 46 are provided to create motion and/or vibration sufficient to move target 38 relative to UV LED so as to provide differing illumination of the target over time, so as to reduce or eliminate non-uniform irradiation of the target 38. If desired, such movement can be of a frequency and amplitude to turn over, rotate, etc., the target 38 so as to provide coverage of more if not all surfaces of the target. Use of a highly reflective chamber 30 as described above assists with improving UV LED radiation of such coverage so that more uniform coverage is achieved.

Configuring chamber 30 so that at least the center portion near UV LED 40 has a predetermined spacing of H1 greater than a height h of target 32 enables the one or more actuators 46 provided to move target 32 relative to support 44. Further, if at least H1, if not H2 or other portions are greater than at least 1.25 or at least 1.5 times h, the ability to achieve such movement may be enhanced. Moreover, having at least H1 be greater than h by such amounts can assist substantially in allowing target 32 to flip over due to the vibrations of the at least one actuator 46. If target 32 is a hearing aid, such devices come in many styles (e.g., in the canal, completely in the canal, in the ear, behind the ear, receiver in canal, receiver in ear, open fit, etc.). Such devices vary in size, both within styles and between styles, as do other target such as earbuds, Bluetooth devices, etc. Thus, H1 may be as small as 0.5 inches for relatively smaller targets, but H1 more likely to allow for vigorous movement and/or flipping of target 38 or use with a larger target or a range of differently-sized targets at higher sizes, such as 1.0 inches, 1.25 inches, 1.5 inches, 2.0 inches, 3.0 inches, or more, etc. A balancing of H1 to H2 ratios, taking into account the curvature of UV plate 32 or chamber top, depending on desired reflection pattern and overall size of device 20, can also factor into the dimensioning of H1, H2, curvature of UV plate 32, etc. For example, H1 can be greater than H2, 1.25 times greater, 1.5 times greater, or more, etc.

If desired, one or more actuators 46 can be mounted at or in contact with any location within device 20, such as base 24, lid 26, surfaces 32,34,36, UV LED/heat sink assembly 40/42, support 44, etc. Such actuators can be used to move/deform/vibrate the reflective surfaces, the UV LED, the support, etc.

The UV LED 40 selected as the UV emitter can be a single UV LED or multiple UV LED's, or one or more UV LED's with multiple chips, with a common or independent control of each UV LED and/or chip. UV LED peak emission wavelength is in UV-C spectral range with a wavelength range of between 200 nm to about 285 nm, however, ranges may also be about 200 nm to about 235 nm and about 255 nm to about 285 nm which are effective against certain microorganisms. While susceptibility to UV light varies, exposure to UV energy for about 20 to about 34 milliwatt-seconds/cm2 is adequate to deactivate approximately 99 percent of most pathogens. Other parameters may be used, however. As discussed below, a controller can be used to alter the timing and power of the UV LED.

Alternatively, the UV emitter(s) may further include or instead include a super-luminescent (SLED or SLD), a laser diode (LD), or any other UV source providing emissions suitable for control of microorganisms, as mentioned above, whether entirely within the above spectral ranges or within other ranges.

A super-luminescent diode is an edge-emitting or vertically-emitting semiconductor light source. It combines the high power and brightness of laser diodes with the low coherence of conventional light-emitting diodes. A super-luminescent light emitting diode is, similar to a laser diode, based on an electrically driven pn-junction that, when biased in forward direction, becomes optically active and generates amplified spontaneous emission (stimulated emission) over a wide range of wavelengths. The peak wavelength and the intensity of the SLED depend on the active material composition and on the injection current level. SLED's are designed to have high single pass amplification for the spontaneous emission generated along the waveguide but, unlike laser diodes, insufficient feedback to achieve lasing action. This is obtained very successfully through the joint action of a tilted waveguide and anti-reflection coated facets.

A laser diode is a semiconductor device that emits light through a process of optical amplification based on the stimulated emission of electromagnetic radiation. The main difference compared to SLEDs is a strong feedback that occurs in the optical cavity in between anti-reflection coated facets designed for multi-pass amplification. Optical amplification occurs in the cavity under injected electric current sufficient to create so called "inversion-population."

Support 44 may be a continuous perforated holder, as illustrated to allow light transmission therethrough. Alternatively, it may be a transmissive, transparent, and/or or UV reflective material. Thus, support 44 may be a discontinuous UV reflective member including material selected from Aluminum, UV-enhanced Aluminum, Aluminum Oxide Aluminum, and UV-enhanced Aluminum Oxide Aluminum, or it may include a UV-transparent polymer selected from FEP, EFEP, PLA, and LDPE. Support 44 may include a discontinuous member, a perforated member, a grid, a mesh, a weave, etc. Support 44 may include a plurality of openings for transmitting emitted UV radiation therethrough, as well as allowing airflow therethrough. Support 44 may be removable (e.g., by removing screws, by a snap fit, etc.) for cleaning the support, plate 34, and/or base 24.

A fan 54 may be located within housing 22, for example within base 24, for pulling air through housing 22 past target 38 to assist in drying the target. One flow path is as follows: lid cover 56 may have openings 58, first plate 32 may have openings 60, support 44 may have openings 62, plate 34 may have openings 64, and base 24 may have openings 66. However, other openings and flow paths are possible thorough housing 22 upstream and downstream of fan 54. The air-flow may go in either direction (lid-to-base or base-to-lid), or may be through lid only or base only, and need not go past or through support 44. Thus, if desired, fan 54 may pull air past UV LED 40 and remove heat generated by the UV LED (from heat sink 42 if present) to assist in drying target 38. Fan 54 may be operated continuously, intermittently, before or after the UV LED, based on a sensed temperature, moisture or humidity level, etc., and may be stopped, started, adjusted or modulated as desired.

Device 20 may include at least one UV radiation monitoring structure 68, which may be a sensor (as shown) or may be a window (not shown) though base 24 and/or lid 26. Sensor 68 located within housing 22 may be for example a photodetector for sensing UV radiation and communicating a corresponding signal to a controller 70 located within the housing. Sensor 68 may be a single UV photodetector and/or multiple UV photodetectors with different spectral responses. UV LED emission of parasitic visible light, predominantly close to blue, yellow, or white for example may be monitored. If UV monitoring structure 68 is a window, it may be a UV blocking window located in the housing with a material that transmits a parasitic visible light emitted by the UV LED, or it may include a fluorescing material activated by the UV LED to transmit a fluorescent visible light. The window may block UV radiation and transmit white light or visible light with wavelength longer than 400 nm. Lack of sensed emission, visible light, fluorescence, etc., indicates failure of the UV LED radiation source and/or the device in general. Also, indicator LED's 78, 80 may be provided on outside of housing 22 to indicate for example, power on, UV LED on, fan on, cleaning in progress, cleaning complete, etc.

Device 20 may include elements for vibration isolation and UV blocking. O-rings 72,74 may be located in base 24 and lid 26 to reduce vibration of the device. Vibration isolation pads 76 are attached to the bottom of base 24. O-rings 72,74 may also assist in blocking UV radiation from escaping radially out of device 20, and a small annular wall 75 on one or both of base 24 and lid 26 may also assist in such blocking.

Figure 9:
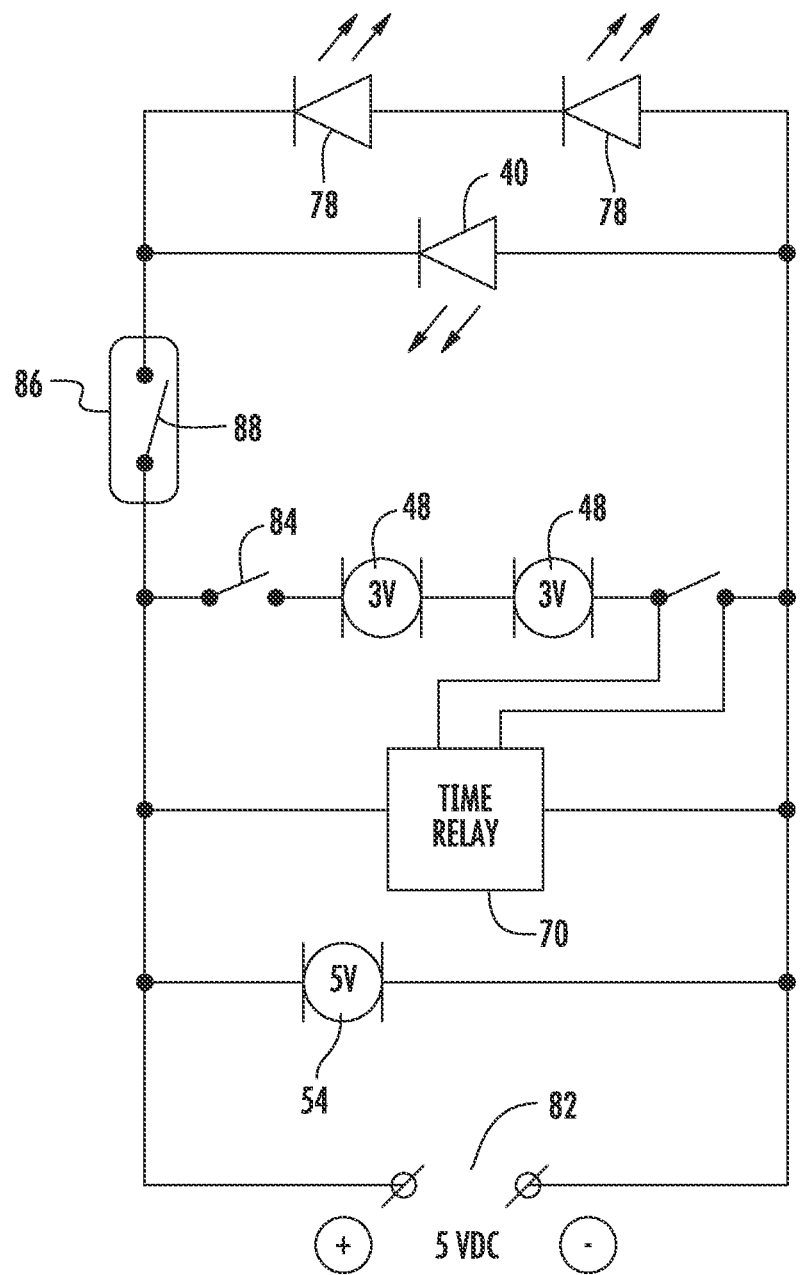
FIG. 9 is an example of one possible circuit diagram for the device of FIG. 1.

The electrical connections of elements of device 20 are omitted for clarity, but are shown schematically in FIG. 9. As illustrated, controller 70 may be provided as hard-wired circuitry on a printed circuit board within the housing for controlling the at least one UV LED 40, actuator 46, and the device in general. Device 20 may be powered via a USB-type connector providing 5VDC power. The device could also be powered by an external battery or an internal rechargeable battery. Fan 54 may also be 5VDC, and may draw about 0.2 A at 10,000 rpm, moving 2.6 cfm. Vibro-actuator motors 48 may operate at 3VDC and 0.05 A, to provide vibrations at 120-150 HZ with an amplitude of 0.5 g. On-off switch 84 may be provided on housing 22 for the user to operate. Controller 70 may include a timer relay with programming in memory, or solid state or other logic control to control the operation of the disclosed elements. A cover-open sensor 86 may be provided to turn off device 20 in total, or just UV LED 40, or to simply provide a signal to controller 70 if lid 26 is raised. Sensor 86 may include a reed switch 88 and a magnet 90 or other sensor, such as electronic, electromagnetic, optical, physical, etc. Sensors may be provided throughout device 20 as noted above (but not shown in FIG. 9) and connected to the controller 70 as needed.

Controller 70 may send signals to UV LED 40 to control at least one of the intensity, wavelength, duration and schedule of the emitted UV radiation. A temperature sensor may be provided in communication with controller 70, with the controller sending control signals to UV LED 40 based on a signal received from the temperature sensor so as to achieve a desired temperature. Controller 70 may control a speed of fan 54 so as to achieve a desired air flow through the housing. Controller 70 can be used to operate device 20 sufficiently to sanitize target 38. For hearing aid devices, 15-20 minutes may be sufficient, although longer times may be used. For certain organisms, cycling may improve disinfection rates to avoid photo-reactivation. Device 20 can be run overnight, at a set time (if controller 70 and/or device 20 includes a clock/timer function). Accordingly, many different modes of operation may be selectable, either by hard-wiring or programming them into controller 70, or by providing switching or other user input-output devices for user indication of desired operation.

According to certain other aspects of the disclosure, a method for cleaning a target 38 may include the steps of supporting the target 38 on a support 44 in a chamber 30 in a housing 22, the chamber defined by first and second UV reflective plates 32,34; operating at least one UV LED 40 attached to housing 22 and positioned to emit UV radiation into chamber 30 so that the UV radiation illuminates target 38; and operating an actuator 46 to modify the UV radiation illumination of target 38 while UV LED 40 is operated. Actuator 46 may move target 38 relative to support 44 while operating, and/or may deform and thereby change a curvature of at least one of first and second UV reflective plates 32,34 while operating, and/or may move UV LED 40 relative to housing 22 when activated.

It should be understood that device 20 and accordingly the above-described method may be modified in various ways, such as, for example, by changing the shape of or eliminating any one, two, or all of UV reflective plates 32,34,36, by modifying the surface profile of support 44 (for example, by including a depression to help keep the target centered beneath the UV LED), by providing vertical vibration (in combination or alone) sufficient to cause the target to flip over on the support, by configuring actuator mount 50 in different ways or by connecting the actuator mount to different elements (including support 44), by providing an air flow from fan 54 (or an additional fan) to help keep the target centered beneath the UV LED, by using or adding an alternate UV emitter, etc.

Figure 11:
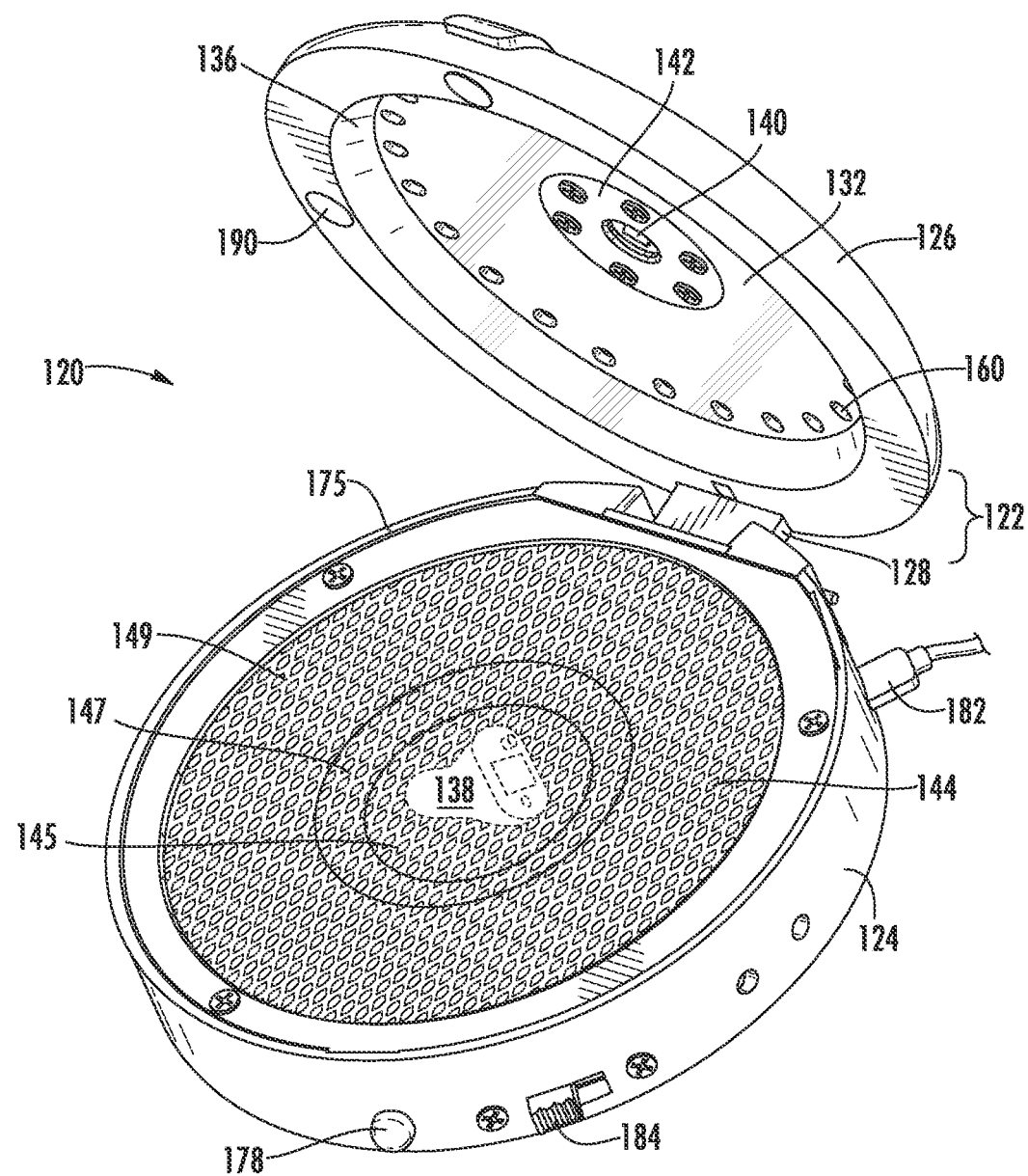
FIG. 11 is a schematic view showing a modified version of the device of FIG. 1.
Figure 12:
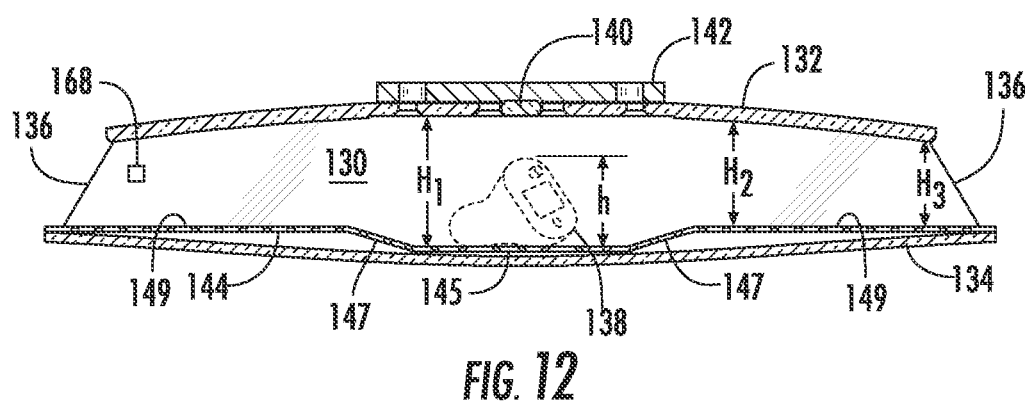
FIG. 12 is a close-up cross-sectional view of a portion of the chamber portion of the device of FIG. 11.

FIGS. 11 and 12 show an additional embodiment of a device 120 for cleaning a target 138. For brevity and clarity, like and similar reference numerals in the 100 series are used in the figures to refer to like and similar elements of device 120, although not all mentioned herein. Differences between embodiments will be highlighted.

As illustrated, device 120 includes a housing 122, a chamber 130 within the housing having a top defined by UV reflective plate 132, and a bottom defined by UV reflective plate 134. The UV emitter, in this case an LED 140 but also possibly adding or substituting another type of UV emitter as noted above, is located to emit UV radiation into chamber 130, and a support 144 is attached to housing 122. Support 144 is located in the chamber 130 so as to be spaced from the top by a predetermined distance (varying between H1, H2, and H3) sufficient to allow target 138 (with height h) to flip within the chamber.

Support 144 is configured for locating target 138 so that the UV radiation illuminates the target. Support 144 may be flat as in device 20 above, or it may be non-flat as in device 120. As illustrated in FIGS. 11 and 12, support 144 includes a top surface defining a depression 145 configured for receiving target 138 and gravitationally urging the target toward a location in which the UV radiation illuminates the target (e.g., toward UV LED 140). As shown, depression 145 is located generally vertically beneath UV LED 140 in chamber 130. Slanted sides 147 around depression angle upwards to periphery 149. Use of slanted sides 147 assist with gravitational urging of target 138 toward depression 145 from periphery and/or help maintain the target within the depression as vibration occurs. Such configuration to assist with maintaining target 138 in position to receive UV radiation can be helpful in efficiently irradiating the target. Such configuration can be particularly useful, but is not required in all embodiments, in devices in which actuators operate vigorously enough to flip over target 138 within chamber 130.

It should be understood that support 144 can be configured in other non-flat shapes than elements 145/147/149 as illustrated to assist with locating target 138. For example, and of portions 145/147/149 need not be linear or flat in cross-section as illustrated. Support 144 could be continuously curved from periphery of support 144 toward center of the support with a curve approximating or with greater radius of curvature than plate 134. Portions 145/147/149 can be of different radius on support 144 relative to each other or support 144 in general. Portions 145 and 147 could be combined into a continuous curve or conical slant rather than the illustrated conical slant (147) and flat (145). If desired, housing 122 may be configured so that the predetermined distance (H1, H2 and/or H3) is adjustable, wherein the location of some or all of support 144 is adjustable relative to the top of chamber 130. Such could be achieved by providing a support 144 movable relative to base 124, or a single part or multi-part support that is itself reconfigurable, bendable, slidable, articulable, etc.

These and other modified configurations cold be used with support 144 to assist in locating target in a desired orientation nearer UV LED, although a flat support as in support 44 could be used as well. Also, in some aspects as in the claims below, a reflective plate such as plate 134 could be considered the support, and a separate support such as element 144 could be eliminated. Use of structures to assist in locating target 138 nearer UV LED 140 can provide better instantaneous radiation coverage of the target. Accordingly, a shorter total duration of illumination may be required, a weather LED may be employed, etc., to save time, electricity, etc., in some aspects.

If desired, a protecting coating may be provided on or between one or more of UV reflective plates 132,134,136, in particular, any plate that might be contacted by target 138 during vibrational moving. Thus, a protecting covering such as a continuous or discontinuous UV transparent polymer, coating, etc. can be applied to any surface desired, including those that might be contacted by target 138. Such includes an embodiment where plate 134 itself acts as support, as noted above.

If desired, openings in plate 134 (either in addition to openings such as 64 in FIG. 2, or by moving openings 64) may be provided radially outwardly of support portions 145 and/or 147 (if present) to assist in moving air output by a fan (such as fan 74) inwardly, thereby assisting in maintaining target 138 centrally in a desired position relative to UV LED 140. A second fan may be provided for such air flow, with a second and/or different flow path as compared to fan 74. Also, the target-aligning flow may pass through other portions of base 124 and/or lid 126, and not necessarily through plate 134.

One or more actuators as discussed above may be employed with device 120. Actuators may be attached for direct movement of plates 132, 134, support 144, base 24, lid 26, etc. Actuator(s) may operate as above, and may operate with sufficient frequency and amplitude so as to move and/or flip over target 138 on support 144 during operation.

A controller as discussed above may be employed for controlling UV 140 LED and the actuator(s), wherein the controller sends signals to the UV LED to control at least one of the intensity, wavelength, duration and schedule of the emitted UV radiation, wherein the controller sends signals to the actuator to control at least one of the frequency, amplitude, duration and schedule of the vibration of the actuator.

Figure 13:
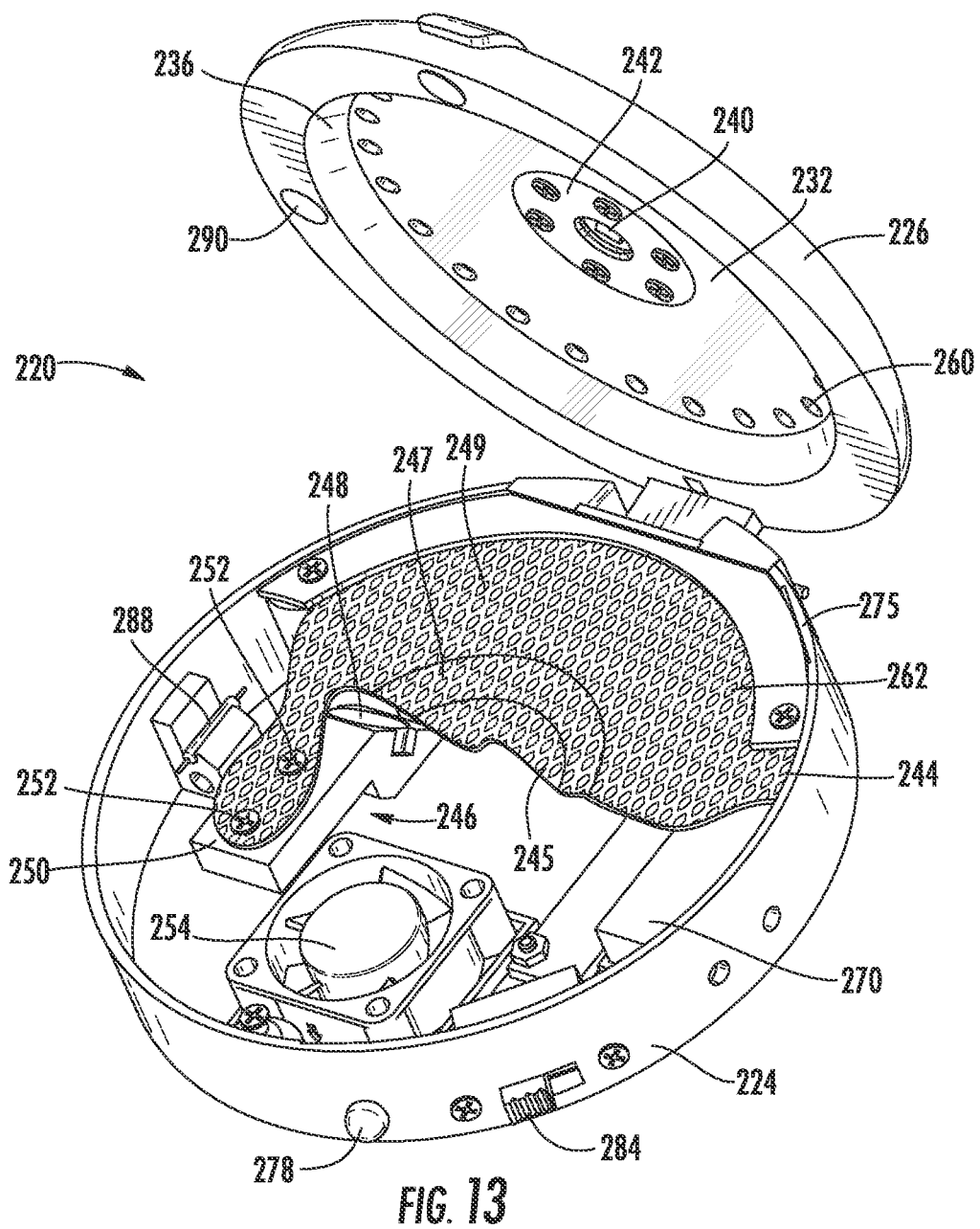
FIG. 13 is a schematic view showing another modified version of the device of FIG. 1.

FIG. 13 shows a modified device 220 in which plate 134 has been eliminated and actuator housing 250 is vibrationally attached directly to support 244 by screws 252. Surface 232 and optionally surface 236 may be UV reflective, although they need not be in all configurations. Support 244 includes portions 245/247/249, although all options and alternatives for the support mentioned above could be employed. In particular, due to the elimination of plate 134, support 244 could be made into a more continuous or fully continuous plate rather than a grid, and/or could be made highly reflective to assist in illuminating target 138. If support 244 is sufficiently reflective, it may be the only reflective surface within device 220. Moreover, support 244 itself need not be reflective, nor are any other surfaces required to be reflective in all aspects of the disclosure. Of course, with lessening or no reflective surfaces, device 220 may have to operate longer, with more or stronger UV emitters, or other compensations may have to be made to clean target 138 as completely as in other configurations.

Figure 14:
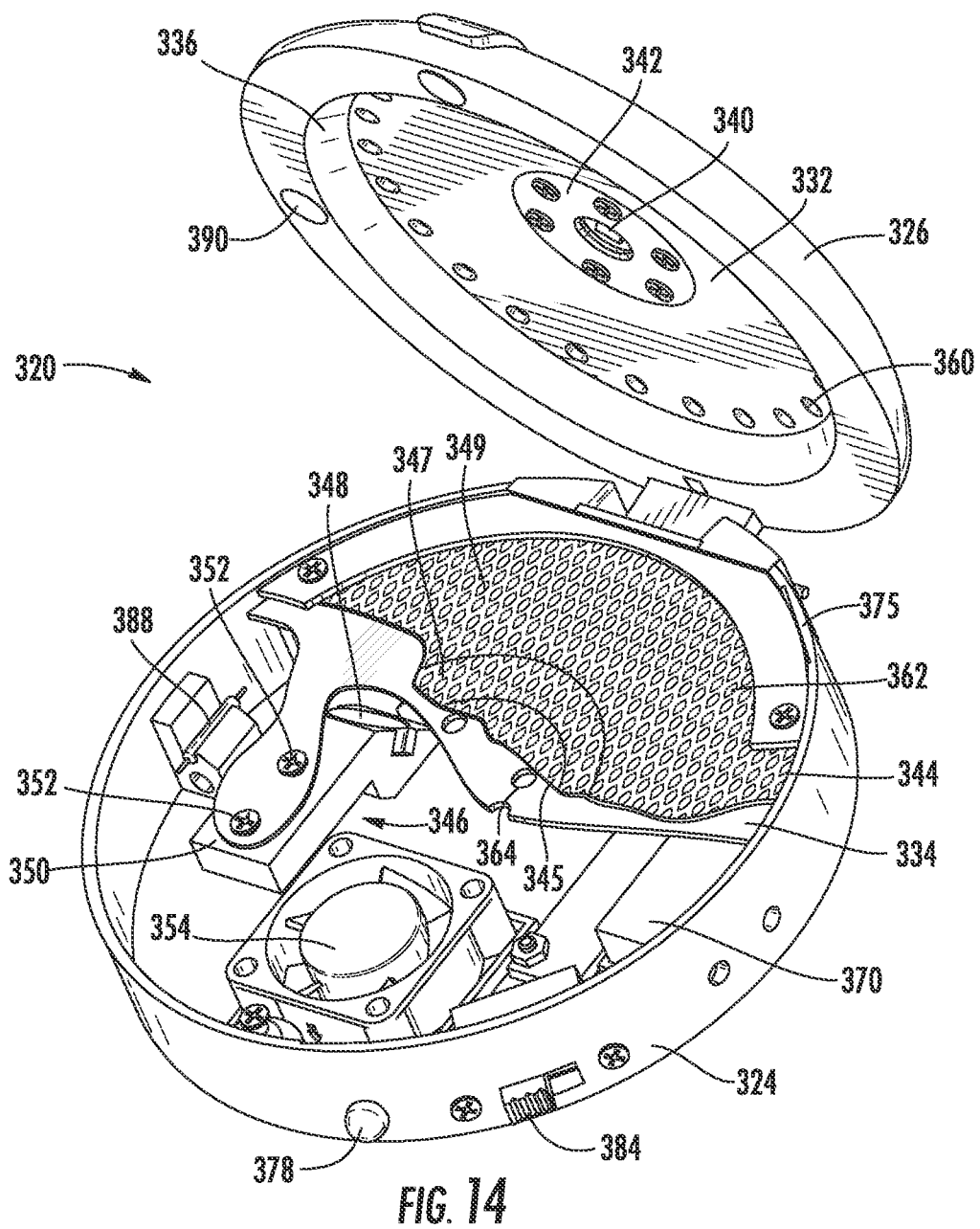
FIG. 14 is a schematic view showing another modified version of the device of FIG. 1.

FIG. 14 shows another alternative device 320 in which lower reflective plate 334 is provided beneath support 344 and is attached to actuator mount 350 by screws 352. Again, support 344 may or may not be reflective. Support 344 is shown with portions 345/347/349, but may be modified as above to have other configurations. Surfaces 332 and 336 are not reflective, but one or both could be.

Figure 15:
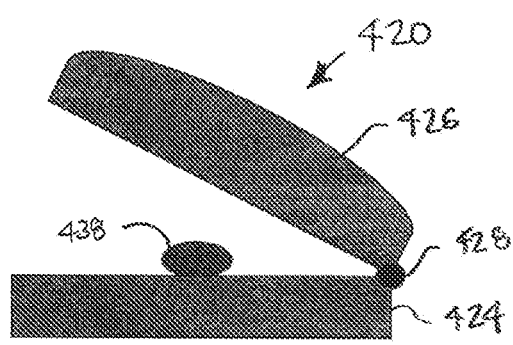
FIG. 15 is a schematic side view showing another modified version of the device of FIG. 1.
Figure 16:
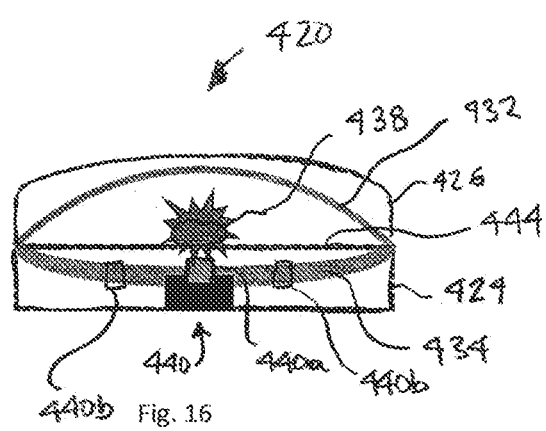
FIG. 16 is a schematic cross-sectional view of the device of FIG. 15.
Figure 17:
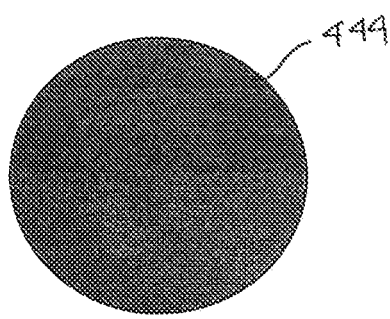
FIG. 17 is a schematic top view of the holding plate of the device of FIG. 15.

FIG. 15-17 schematically show another alternate device 420 with a base 424 and lid 426 connected by a hinge 428. A light source 440 for illuminating the target 438 within a light chamber is mounted in the base 424, beneath a holding plate (support) 444 for holding the target 438. No light source is in the lid. The light source may be one or more of an LED, UV LED, etc., as described above, or the light source may be the outlet of a waveguide for transmitting light from, for example, a UV LED, to a location in which the light can be introduced into the chamber. The light source 440 may be a single localized source 440a, or may include multiple sources 440a and/or 440b. One or more reflective plates 432 and/or 434 may be provided at a top and bottom of the chamber (within lid 426 and base 424, respectively) for reflecting light to improve coverage on the target 488. Placing the light source 440 only in base 424 locates it with other electronics, simplifies electrical connection to the light source, and prevents wear and tear on connecting electronics that might pass through or alongside the hinge between the base and lid.

Figure 18:
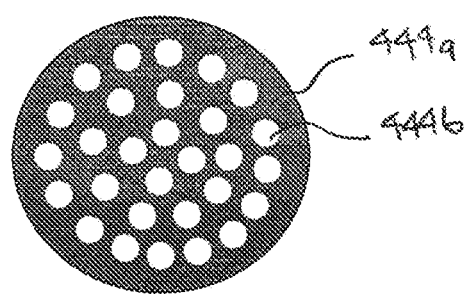
FIG. 18 is a schematic top view of an alternate holding plate for the device of FIG. 15.

As shown, the holding plate/support 444 in FIG. 17 as solid (at least partially translucent/transparent), but it may alternatively be a perforated element 444a with openings 444b, as in FIG. 18 to improve light or airflow transmission, or to allow drainage.

Figure 19:
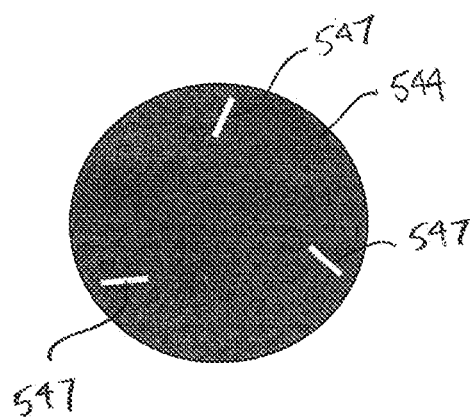
FIG. 19 is a schematic top view of an alternate, rotatable holding plate having fins adaptable to other embodiments above.
Figure 20:
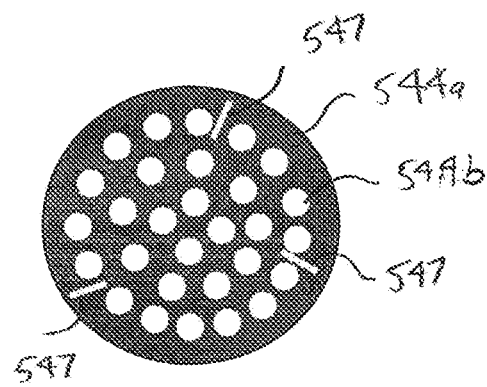
FIG. 20 is a schematic top view of another alternate rotatable holding plate of the assembly of FIG. 19.
Figure 21:
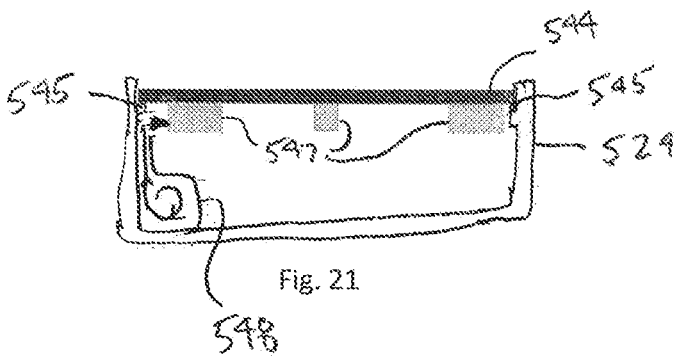
FIG. 21 is a schematic side view showing use of the rotatable holding plate of FIG. 19 in a base of a device as above with a fan.

FIGS. 19-21 show another modified holding plate assembly that could be incorporated into any of the embodiments above. As shown in FIG. 21, holding plate 544 is rotatable on bearings 545 mounted to base 524. Plate 544 includes at least one (three shown) fin 547 that can cooperate with one or more fans 548 in base 524 to effect the rotation of the holding plate to the base. FIG. 20 shows alternative plate 544a with openings 544b for air, light, or liquid transmission. Either type of holding plate may be mounted around its perimeter to the base or structure attached to the base (as shown) and/or mounted centrally (not shown). Thus, the fan and the fins if included, comprise a means for rotating the support relative to the base so that the target moves relative to the at least one UV emitter in the base. Fins are not strictly required, and thus may be replaced by other structures that are inherently part of or that extend from holding plate, whether formed unitarily or added, so that impinging air from one or more fans causes the relative rotation.

Figure 22:
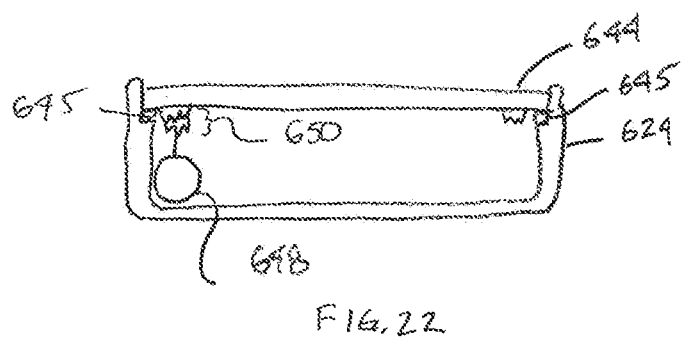
FIG. 22 is a schematic side view of an alternative to FIG. 21 adaptable to above embodiments, wherein a holding plate is rotatable via a motor in the base.

Alternatively, as shown in FIG. 22, a motor 648 can be provided in the base to effect rotation of the bottom reflector and/or holding plate 644 by mechanical drive connection 650 (geared, frictional, belts and pulleys, etc.), rather than via airflow. Also, actuators such as those provided for vibration noted above can be configured and aligned with a movable holding plate or reflective surface to achieve relative rotation between such structure and the base. Such alternative structures also may comprise a means for rotating the support relative to the base so that the target moves relative to the at least one UV emitter.

Rotation can be employed to allow different areas of the target to be covered by the light from the light source. If desired, the bottom reflective plate, not the holding plate could instead be rotated relative to the base. Also, if fans are provided for cooling and/or drying, rotation allows such effects to be made more uniform via the rotation. Optionally a cleaning liquid such as water, a disinfectant, alcohol, etc., may be sprayed by a pump within the base into the chamber and/or on to the target for further cleaning. If so, fans in the base may assist with drying the target and/or chamber, and rotation may assist with drying of such cleaning liquids. As shown in FIGS. 17-21, the holding plate may be continuous or perforated, as discussed above.

It should be kept in mind that the various options with the various embodiments noted above regarding vibration, number and location of reflective surfaces, plate shape, plate perforation, transmissivity, etc., can all be applied to the devices of FIGS. 15-22 or vice versa.

Otherwise, the following parameters may be adopted with the FIG. 15-22 embodiments or the earlier embodiments.

One or more of the UV reflectors may have reflectivity of more than 0.1% in the wavelength range of about 200-300 nm. Also, the holding plate may have UV transparency more than 0.1% in the wavelength range about 200-300 nm. If the holding plate is perforated, the UV transparency may be more than 0.1% in the wavelength range of about 200-300 nm, and perforation pattern (opening) size may be less than the size of the object. Although, it should be understood that the holding plate need not be UV transparent. UV transparency and/or reflectivity also does not necessarily have to be more than 0.1% over the entire 200-300 nm range. Transparency and/or reflectivity may be less than that in certain wavelength range(s) except for the disinfection wavelength.

Fans and actuators are optional, and various types of similar and different curvatures of the top and bottom reflectors could be employed for optimized illumination of the target. The curvature of one or more reflectors could be changed by one or more actuators. A surface of one or more of the reflectors and/or the holding plate may be uneven, for example rough surface, polished surface, etc., to provide light diffusion and/or scattering for more uniform illumination of the target. The surface of UV reflector(s) and/or holding plate maybe patterned with pattern size comparable to the disinfection wavelength of light being used.

The UV LED light may be coupled to the chamber through one or more holes in the bottom reflector and/or through a UV transparent window in the bottom reflector. The bottom UV reflector can be (i) a reflecting material, (ii) a UV transparent material with at least one side covered with UV reflecting coating; or (iii) a multi-layered structure with matching UV reflectance/transparency for optimal light waveguiding at disinfection wavelength of light being used. The UV LED light may be coupled to the chamber via waveguiding and multiple reflections inside the bottom reflector with light escape to the chamber through the top surface of the reflector and/or the holding plate.

In view of the above, devices and methods are disclosed in FIGS. 11-22 and discussed in relation thereto modifying or adding to the disclosed subject matter of FIGS. 1-10. Aspects from each of the embodiments may be used apart from the remaining aspects of their respective embodiments and may be combined in various ways with other aspects of this disclosure. Thus, the disclosed devices and methods may incorporate changing the shape of or eliminating any one, two, or all of the UV reflective plates by modifying the surface profile and/or reflectivity of the support, by providing vertical vibration (in combination or alone) sufficient to cause the target to flip over on the support, by the configuring actuator mount in different ways or by connecting the actuator mount to different elements, by providing an air flow from fan (or an additional fan) to help keep the target centered beneath the UV emitter, etc.

While preferred embodiments of the invention have been described above, it is to be understood that any and all equivalent realizations of the present invention are included within the scope and spirit thereof. Thus, the embodiments depicted are presented by way of example only and are not intended as limitations upon the present invention. Thus, while particular embodiments of the invention have been described and shown, it will be understood by those of ordinary skill in this art that the present invention is not limited thereto since many modifications can be made. Therefore, it is contemplated that any and all such embodiments are included in the present invention as may fall within the literal or equivalent scope of the appended claims.

We claim:

1. A device for cleaning a target comprising:
    a housing including a base and a lid, the base having a bottom wall and a side wall defining an interior area therein;
    a first UV reflective plate located in the lid and a second UV reflective plate located in the base;
    a chamber being defined within the housing between a bottom side of the first UV reflective plate and a top side of the second UV reflective plate;
    a plurality of UV emitters attached to the housing, the UV emitters being positioned to emit UV radiation into the chamber, all of the UV emitters being located in the base of the housing, and none of the UV emitters being located in the lid of the housing;
    a support having a plate shape defining a perimeter edge, the support being attached to the base with the perimeter edge in contact with the side wall, the support being located in the chamber and above the UV emitters, the support configured for locating the target so that the UV radiation illuminates the target, the support being at least partially translucent and/or is perforated for allowing at least some of the UV radiation to pass therethrough;
    a fan in the base, at least one fin being attached to a bottom surface of the support, an airflow from the fan impinging on the at least one fin to rotate the support relative to the base,
    wherein the UV emitters include a first UV emitter centrally located beneath the support within the base and at least one second UV emitter spaced radially from the first UV emitter, and
    wherein the UV emitters, first UV reflective plate, second UV reflective plate, and the support are configured so that the UV radiation emitted from the UV emitters in the base is transmitted to and reflected within the chamber to clean the target.

2. The device of claim 1, wherein the base and the lid are attached together by a hinge.

3. The device of claim 1, further including at least one actuator in the base for creating vibration sufficient to move the target relative to the support.

4. The device of claim 1, wherein rotation of the support via the fan causes the target to be moved relative to the first UV emitter and the at least one second UV emitter in the base.

5. The device of claim 1, wherein the support includes a top surface defining a depression in a center thereof configured for receiving the target and gravitationally urging the target toward a location in which the UV radiation illuminates the target.

6. The device of claim 1, including three of the second UV emitters spaced around the first UV emitter.

7. The device of claim 1, wherein the first UV emitter and the second UV emitter each include one of an LED, a UV LED, or a waveguide outlet.

8. A device for cleaning a target comprising:
    a housing including a base and a lid;
    a chamber within the housing having a top within the lid, a bottom within the base, and at least one UV reflective plate;
    at least one UV emitter attached to the housing and positioned to emit UV radiation into the chamber, all of the at least one UV emitters being located in the base of the housing and none of the at least one UV emitters being located in the lid of the housing;
    a support attached to the housing and located in the chamber, the support configured for locating the target so that the UV radiation illuminates the target; and
    a fan in the base, at least one fin being attached to a bottom surface of the support, an airflow from the fan impinging on the at least one fin to rotate the support relative to the base.

9. The device of claim 8, wherein the at least one UV reflective plate is located adjacent the top of the chamber above the support in the lid.

10. The device of claim 8, wherein the at least one UV reflective plate is located adjacent the bottom of the chamber below the support in the base.

11. The device of claim 8, wherein the at least one UV reflective plate includes a first UV reflective plate located adjacent the top of the chamber above the support in the lid and a second UV reflective plate located adjacent the bottom of the chamber below the support in the base.

12. The device of claim 8, wherein the base and the lid are attached together by a hinge.

13. The device of claim 8, further including at least one actuator in the base for creating vibration sufficient to move the target relative to the support.

14. The device of claim 8, wherein rotation of the support via the fan causes the target to be moved relative to the at least one UV emitter in the base.

15. The device of claim 8, wherein the support includes a top surface defining a depression in a center thereof configured for receiving the target and gravitationally urging the target toward a location in which the UV radiation illuminates the target.

16. The device of claim 8, wherein the at least one UV emitter includes a first UV emitter centrally located beneath the support within the base and at least one second UV emitter spaced radially from the first UV emitter.

17. The device of claim 16, including three of the second UV emitters spaced around the first UV emitter.

18. The device of claim 16, wherein the first UV emitter and the second UV emitter each include one of an LED, a UV LED, or a waveguide outlet.

19. The device of claim 8, wherein the support is at least partially translucent and/or is perforated for allowing at least some of the UV radiation to pass therethrough.

\* \* \* \* \*